United States Patent
Werpy et al.

(10) Patent No.: US 6,841,085 B2
(45) Date of Patent: Jan. 11, 2005

(54) HYDROGENOLYSIS OF 6-CARBON SUGARS AND OTHER ORGANIC COMPOUNDS

(75) Inventors: Todd A. Werpy, West Richland, WA (US); John G. Frye, Jr., Richland, WA (US); Alan H. Zacher, Kennewick, WA (US); Dennis J. Miller, Okemos, MI (US)

(73) Assignee: Battelle Memorial Institute, Richland, WA (US); part interest ( * ) Notice: Subject to any disclaimer, the term of this patent is extended or adjusted under 35 U.S.C. 154(b) by 281 days.

(21) Appl. No.: 10/000,836

(22) Filed: Oct. 23, 2001

(65) Prior Publication Data

US 2003/0119952 A1 Jun. 26, 2003

(51) Int. Cl.[7] ............................ C07C 31/18; C09K 3/00
(52) U.S. Cl. ......................... 252/1; 514/501; 514/724; 514/777; 568/861; 568/863
(58) Field of Search ..................... 524/115; 568/863, 568/861, 86; 514/501, 724, 777; 252/1

(56) References Cited

U.S. PATENT DOCUMENTS

| | | | |
|---|---|---|---|
| 2,852,570 A | 9/1958 | Conradin et al. | 260/635 |
| 3,030,429 A | 4/1962 | Conradin et al. | 260/635 |
| 4,338,472 A | 7/1982 | Sirkar | 568/861 |
| 4,366,332 A | 12/1982 | Chao et al. | 568/863 |
| 4,401,823 A | 8/1983 | Arena | |
| 4,404,411 A | 9/1983 | Tanikella | 568/861 |
| 4,476,331 A | 10/1984 | Dubeck et al. | 568/861 |
| 4,496,780 A * | 1/1985 | Arena | 568/861 |
| 5,326,912 A | 7/1994 | Gubitosa et al. | 568/861 |
| 5,354,914 A | 10/1994 | Gubitosa et al. | 568/861 |
| 5,496,786 A * | 3/1996 | Gubitosa et al. | 502/182 |
| 5,543,379 A * | 8/1996 | Gubitosa et al. | 502/184 |
| 6,291,725 B1 | 9/2001 | Chopade et al. | 568/861 |
| 6,479,713 B1 * | 11/2002 | Werpy et al. | 568/863 |
| 6,677,385 B2 * | 1/2004 | Werpy et al. | 514/738 |

FOREIGN PATENT DOCUMENTS

WO    WO 01/66499 A1    9/2001

OTHER PUBLICATIONS

Zhang, Z., et al. "Aqueous–Phase Hydrogenation of Lactic Acid to Propylene Glycol." p. 89–98. 2001.

* cited by examiner

Primary Examiner—Cephia D. Toomer
(74) Attorney, Agent, or Firm—Wells St. John P.S.

(57) ABSTRACT

Methods for hydrogenolysis are described which use a Re-containing multimetallic catalyst for hydrogenolysis of both C—O and C—C bonds. Methods and compositions for reactions of hydrogen over a Re-containing catalyst with compositions containing a 6-carbon sugar, sugar alcohol, or glycerol are described. It has been surprisingly discovered that reaction with hydrogen over a Re-containing multimetallic catalyst resulted in superior conversion and selectivity to desired products such as propylene glycol.

31 Claims, 7 Drawing Sheets

HYDROGENOLYSIS OF 6-CARBON SUGARS AND OTHER ORGANIC COMPOUNDS

STATEMENT OF GOVERNMENT RIGHTS

This invention was made with Government support under contract DE-AC0676RLO 1830 awarded by the U.S. Department of Energy. The Government has certain rights in this invention.

FIELD OF THE INVENTION

The present invention relates to hydrogenolysis of aqueous organic compounds, especially hydrogenolysis of sugars, sugar alcohols and small molecules.

BACKGROUND OF THE INVENTION

Currently, many of the chemicals in common use are derived from petroleum feedstocks. However, petroleum is present in limited underground reserves, and the extraction, transportation, and refining of petroleum can have severe environmental consequences.

Bio-based feedstocks, on the other hand, can be obtained from plants and can be processed by biological processes such as fermentation. To more fully utilize bio-based materials, it is often necessary to convert the fermentation products or other bio-based feedstocks into other chemicals that can be used in a variety of processes and products. Thus, it is an object of the present invention to provide new methods of converting sugars, sugar alcohols and other small molecules into a variety of desired chemical products.

For a long time, scientists and engineers have sought to convert sugars and sugar alcohols into other chemical products. For example, Conradin et al. in U.S. Pat. No. 2,852,270 (filed in 1957) reported that for increased production of propylene glycol, hydrogenolysis should be conducted over a Ni/Cu catalyst on a carrier such as magnesium oxide.

In U.S. Pat. No. 3,030,429 (filed in 1959), Conradin et al. stated that hydrogen splitting of saccharose to glycerol and glycols can be carried out in the presence of practically any technically feasible catalyst, provided that sufficient alkali is added to ensure a pH of 11 to 12.5. In one example, it was reported that hydrogenolysis of an aqueous saccharose solution over a nickel-on-kieselguhr catalyst proceeded with an 83% conversion to a product containing 43% glycerol and 25% propylene glycol.

Sirkar in U.S. Pat. No. 4,338,472 (filed in 1981) reported sorbitol hydrogenolysis to produce glycerol over a nickel-on-kieselguhr catalyst in which an alkali promoter was added to the feedstream to control pH and prevent leaching of nickel from the catalyst.

Tanikella in U.S. Pat. No. 4,404,411 (filed in 1983) described the hydrolysis of sorbitol and xylitol in nonaqueous solvents containing at least 10 mole % base. The catalyst used in the examples was nickel on silica/alumina. Distribution of ethylene glycol, propylene glycol and glycerol were reported.

Gubitosa et al. in U.S. Pat. No. 5,600,028 (filed in 1995) discussed the hydrogenolysis of polyhydric alcohols, such as sorbitol, over a ruthenium-on-carbon catalyst. In the examples, Gubitosa et al. reported that 100% of the sorbitol can be converted, with 41 to 51% of the product carbon atoms in propylene glycol.

Despite these and other efforts, there remains a need for new methods of converting sugars and sugar alcohols to smaller molecules that have a variety of uses. There is also a need for novel methods of converting molecules such as sorbitol and glycerol into higher value products such as propylene glycol and 1,3-propanediol. There is especially a need for new methods of such conversions that provide better yield and more desirable product distributions.

SUMMARY OF THE INVENTION

The invention provides a method of hydrogenolysis of an oxygen-containing organic compound, comprising: reacting an aqueous oxygen-containing organic compound with hydrogen at a temperature of at least 120° C., and in the presence of a solid catalyst; where the solid catalyst comprises a Re-containing multimetallic catalyst, and where there is at least 25% as much C—O hydrogenolysis occurs as C—C hydrogenolysis. In some preferred embodiments, at least 100% as much C—O hydrogenolysis occurs as C—C hydrogenolysis. In some preferred embodiments, these percentages (such as 25%) refer to the total amount of hydrogenolysis, in other embodiments, they refer to rates, for example, the rate of C—O hydrogenolysis is at least 25% as fast as the rate of C—C hydrogenolysis. It has been surprisingly discovered that a Ni/Re catalyst is superior to other catalysts.

The present invention also provides a hydrogenolysis method in which a 6 carbon sugar, a 6 carbon sugar alcohol, or glycerol is reacted with hydrogen, at a temperature of at least 120° C., and in the presence of a solid catalyst comprising a rhenium-containing multimetallic catalyst.

In a second aspect, the invention provides a composition of matter comprising: a solid rhenium-containing multimetallic catalyst; water, hydrogen; and a 6 carbon sugar, a 6 carbon sugar alcohol or glycerol.

In another aspect, the invention provides a method of improving the catalytic activity or selectivity of a supported metal catalyst for the reaction of hydrogen with a 6-carbon sugar, a 6-carbon sugar alcohol, or glycerol. In this method, rhenium is incorporated in a metal catalyst to form a rhenium-containing multimetallic metal catalyst. The Re-containing catalyst is reduced prior to, or simultaneous with a hydrogenolysis reaction. Preferably, the reduction is carried out by exposing the catalyst to hydrogen gas. Preferably, the 6-carbon sugar or a 6-carbon sugar alcohol is exposed to hydrogen and a rhenium-containing multimetallic metal catalyst under conditions sufficient to convert at least 40% of the sugar or sugar alcohol to propylene glycol, glycerol, ethylene glycol or any combination thereof. "Improving" means that when tested with a 20 weight % glycerol in aqueous solution with 2 weight % sodium hydroxide, 1200 psi (8.2 MPa) hydrogen in a batch reactor for four hours, the yield of PG is improved by at least 5%, as compared with running the same reaction under the same conditions over each of: the same catalyst without rhenium, the same catalyst without rhenium but containing added weight of metal equal to the weight of rhenium in the improved method, and the same catalyst without rhenium but containing added moles of metal equal to the moles of rhenium in the improved method.

In yet another aspect, the invention provides a method of improving the reaction of hydrogen with a 6 carbon sugar or a 6 carbon sugar alcohol. In this method, the 6 carbon sugar, or a 6 carbon sugar alcohol is exposed to hydrogen and a rhenium-containing multimetallic metal catalyst under conditions sufficient to convert at least 40% of the sugar or sugar alcohol to propylene glycol, glycerol, ethylene glycol or any combination thereof. "Improving" means that at the same conditions where the rhenium-containing multimetallic catalyst results in 80% conversion, the yield of PG is improved by at least 5%, as compared with running the same reaction over each of: the same catalyst without rhenium, the same catalyst without rhenium but containing added weight of metal equal to the weight of rhenium in the improved method, and the same catalyst without rhenium but containing added moles of metal equal to the moles of rhenium in the improved method.

In another aspect, the invention provides a hydrogenolysis method in which a 5 carbon sugar, a 5 carbon sugar alcohol, lactate or lactic acid is reacted with hydrogen, at a temperature of at least 120° C., and in the presence of a solid rhenium-containing multimetallic catalyst.

In yet a further aspect, the invention provides a composition of matter comprising: a solid rhenium-containing multimetallic catalyst, water, hydrogen, and a 5 carbon sugar, a 5 carbon sugar alcohol; lactate or lactic acid.

In another aspect, the invention provides a method of making propylene glycol, comprising: reacting a composition comprising lactate or lactic acid with hydrogen in the presence of a catalyst; where acid is added to the composition prior to the step of reacting; where the lactate or lactic acid is converted with a yield of at least 60%; and wherein the PG selectivity is at least 80%.

In a further aspect, the invention provides a method of improving the reaction of hydrogen with a 5 carbon sugar, a 5 carbon sugar alcohol, lactate or lactic acid. In this method, a 5 carbon sugar, a 5 carbon sugar alcohol, lactate and lactic acid is reacted with hydrogen in the presence of a solid, rhenium-containing multimetallic catalyst. In this method, "improving" means that at the same conditions where the rhenium-containing multimetallic catalyst results in 80% conversion, the yield of PG is improved by at least 5%, as compared with running the same reaction over any of: the same catalyst without rhenium, the same catalyst without rhenium but containing added weight of metal equal to the weight of rhenium in the improved method, and the same catalyst without rhenium but containing added moles of metal equal to the moles of rhenium in the improved method.

In a further aspect, the invention provides method of improving the catalytic activity or selectivity of a supported metal catalyst for the reaction of hydrogen with a 5-carbon sugar, or 5-carbon sugar alcohol, or lactic acid. The catalytic activity or selectivity of the supported metal catalyst is improved by incorporating rhenium in said metal catalyst to form a rhenium-containing multimetallic metal catalyst. The catalyst is typically reduced prior to or simultaneous with the reaction of hydrogen with a 5-carbon sugar, or 5-carbon sugar alcohol, or lactic acid. Preferably, the method also includes the step of exposing the sugar, sugar alcohol, or lactic acid to the rhenium-containing multimetallic metal catalyst under conditions sufficient to convert at least 40% of the sugar, sugar alcohol or lactic acid to propylene, glycerol, ethylene glycol or any combination thereof. In this method, "improving" means that, at the same conditions where the rhenium-containing multimetallic catalyst results in 80% conversion, the yield of PG is improved by at least 5%, as compared with running the same reaction over any of: the same catalyst without rhenium, the same catalyst without rhenium but containing added weight of metal equal to the weight of rhenium in the improved method, and the same catalyst without rhenium but containing added moles of metal equal to the moles of rhenium in the improved method.

The invention also includes methods of making 1, 3 propanediol by reaction of the starting materials described herein with hydrogen over Re-containing catalysts. More specifically, this method involves reacting a composition comprising glycerol with hydrogen at a temperature of at least 120° C., and in the presence of a solid rhenium-containing multimetallic catalyst in neutral or acidic conditions.

The invention includes any of the above aspects alone or in combination with any of the details in the following Examples and descriptions of preferred embodiments.

Various embodiments of the inventive methods have been found to provide numerous unexpected results that are superior over prior technologies, including: stability of the catalytic system, high conversions at relatively mild conditions, desired selectivities, high value product distributions such as high concentrations of propylene glycol, high PG selectivity at elevated temperature, production of 1, 3 propanediol, and process control to produce desired products.

The product mixtures that can be derived from the inventive methods offer advantages such as economy and environmentally-friendly derivation from fermented materials. These product mixtures can be used in various applications, for example, as anti-freeze.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

Glossary of Terms

"Rhenium-containing" means that a solid catalyst contains at least 0.5 weight % Re, or that the catalyst contains a sufficient amount of rhenium such that when tested by hydrogenating a solution of 20 wt % sorbitol so that about 80% of the sorbitol is converted to shorter carbon chain products, the selectivity of the catalyst toward producing propylene glycol increases by at least 5% (where increases by 5% refers to absolute improvement, for example the propylene glycol selectivity increases from 20 to 25%.

"Multimetallic" means that the catalyst contains at least two metals (not including metals in the oxide support such as aluminum in alumina). In preferred embodiments, these metals function together to exhibit synergistic effects.

Carbon Molar Selectivity means the percent of carbon in a converted starting material (such as a converted sugar alcohol) that is the form of the selected species. For example, where a solution originally contains 1 mole sorbitol (i.e., 6 mole carbon as sorbitol), and the product contains 0.5 mole sorbitol and 0.25 mole PG (i.e., 0.75 mole carbon as PG), the PG carbon molar selectivity is 25%. In this case, the yield of PG is 12.5%. Unless indicated otherwise, the term "selectivity" in the present descriptions refers to carbon molar selectivity.

DESCRIPTION OF PREFERRED EMBODIMENTS

Feedstocks useful in the present invention contain at least one of a sugar, sugar alcohol, glycerol, lactate or lactic acid. Preferred sugars include the sugars containing 6 carbon chains, such as glucose, galactose, maltose, lactose, sucrose, allose, altrose, mannose, gulose, idose, and talose (referred to herein as "6-carbon sugars"). Another preferred group of sugars are the sugars containing 5 carbon chains, such as ribose, arabinose, xylose, and lyxose (referred to herein as "5-carbon sugars"). It should be understood that under some reaction conditions, especially basic conditions, it is believed that some salt-like interactions may be formed with oxy moieties on the sugars or sugar alcohols and these species, if present, should be included within these definitions.

The feedstocks may be pure materials, purified mixtures or raw materials such as fermentation broth. Some feedstocks are commercially available. Some feedstocks could be obtained as side-products of other processes such as corn processing. Indeed, another advantage of the present invention is that, in some embodiments, the process can use materials that would otherwise be disposed as waste. The feedstocks can also be intermediates that are formed as part of a larger process or in the same process (such as sugar alcohols produced in the initial stage of hydrogenating a sugar). For some bio-based materials, it may be desirable to filter the materials and/or pass them through an ion exchange column or columns.

In preferred embodiments, the feedstocks include water or a nonaqueous solvent. Preferred nonaqueous solvents include methanol, ethanol, ethylene glycol, propylene glycol, n-propanol and i-propanol. Water is especially preferred because of its nontoxicity and prevalence in fermentation processes. The inventive processes have broad applicability, and, in some less-preferred embodiments, the feedstock may include proteins and other materials. Preferably, feedstocks contain 20 to 50 wt % of reactants with the balance substantially composed of solvent.

Catalysts for the hydrogenolysis processes are metal-containing solid catalysts. Preferably the catalysts include a high surface area support material that is selected to resist degradation under the intended reaction conditions. Such support materials are known in the art and may include high surface area oxide supports. Carbon, zirconia and titania (especially in the rutile form) are especially preferred because of their stability in hydrothermal conditions (aqueous solutions at above 100° C. and 1 atmosphere pressure). Supports can also be formed of mixed or layered materials, for example, in some preferred embodiments the support is carbon with a surface layer of zirconia or zirconia mixed with catalyst metals.

For hydrogenolysis reactions, the catalyst preferably contains rhenium. Based on its improvement with all metals tested thus far, it is believed that addition of rhenium will improve the hydrogenolysis performance of any suitable hydrogenation catalyst. In preferred embodiments, the catalyst contains at least one other metal in addition to rhenium. Preferred additional metals include: Ni, Pd, Ru, Co, Ag, Au, Rh, Pt, Ir, Os and Cu, of which Ni, Pd and Ru are especially preferred, for example, Ni/Re, Pd/Re, and Ru/Re. In some embodiments, the most preferred additional metal is nickel.

Preferably, the catalyst contains 0.1 to 5 weight % Re, more preferably 0.5 to 2.5 weight % Re, and still more preferably 0.5 to 1 weight % Re. Also preferably, the catalyst contains 1 to 10 weight % of additional metals, more preferably 2 to 7 weight % additional metals, and still more preferably 2.5 to 5 weight % additional metals. These ranges preferably occur together, for example, 0.5 to 1 weight % Re and 2.5 to 5 weight % additional metals. The foregoing ranges of additional metals are based on experience with Ni and are believed to be appropriate for other metals; however, other metals may have different preferred ranges.

Without intending to limit the scope of the invention, it is believed that the rhenium acts as an oxygen acceptor. The rhenium may also facilitate dispersion and stablilization of the additional metal. It is an important discovery of the present invention that the rhenium and additional metal exhibit synergistic effects. That is, the effects on the catalytic activity and reaction performance are more than could be expected based on the performance of either metal acting alone.

Catalysts are preferably made by incipient wetness impregnation techniques. A porous support may be purchased or prepared by known methods. A catalytic metal precursor is prepared or obtained. The precursor may be prepared, for example, by dissolving a metal compound in water or acid or purchasing a precursor in solution. The precursor may be in the form of a cation or an anion. A typical precursor for nickel may be nickel nitrate dissolved in water. A typical precursor for ruthenium may be ruthenium chloride. A typical precursor for rhenium may be perrhenic acid. Each of the precursor materials may be in liquid or solid form; these particles may also contain other components such as halides, cations, anions etc. In some preferred embodiments, organic solvents are avoided and the precursor impregnation solution is prepared only in water. Conditions for preparing precursor solution will depend on the type of metal and available ligands. In the case of a particulate support, such as activated carbon powders, the support and precursor composition can be mixed in a suspension. The porous support is preferably not coated by a vapor-deposited layer, more preferably the method of making the catalyst does not have any vapor deposition step. A catalyst metal can be deposited subsequent to, or simultaneous with, the deposition of a metal oxide. Catalyst metal components can be impregnated into the support in a single-step, or by multi-step impregnation processes. In a preferred method, the precursor for the catalyst component is prepared in a single solution that is equivalent in volume to the measured amount of solvent that the porous support will uptake to exactly fill all of the pore volume. This solution is added to the dry support such that it is absorbed by the support and fills all of the available pore volume. The support can then be vacuum dried in order to remove the solvent and leave the catalytic metal precursor to coat the surface of the support. Subsequent reduction will reduce the catalytic material to its metallic state or another oxidation state and will often disassociate the metal from its anion or cation used to make the metal soluble. In most cases, the catalyst is reduced prior to use.

In methods of the present invention, hydrogenolysis of sugars and sugar alcohols preferably occurs in a temperature range of 140 to 250° C., more preferably 170 to 220° C. The hydrogenolysis reaction should be conducted under basic conditions, preferably at a pH of 8 to 13, more preferably 10 to 12. Acids, particularly lactic acid, may form during hydrogenolysis and neutralize some of the base. As the reaction progresses, pH approaches neutral and PG selectivity decreases. To ameliorate this problem, additional base can be added to increase pH.

In flow reactors, the hydrogenolysis reaction is preferably conducted at a weight hourly space velocity (WHSV) of 0.3 to 3 kg reactant per kg catalyst per hour. In batch reactors, hydrogenolysis reaction times preferably range from 0.3 to 10 hours.

It has also been discovered that the yield of PG can be improved by neutralizing or acidifying the product mixture resulting from hydrogenolysis and hydrogenating the product mixture under neutral or acidic conditions. Because the hydrogenolysis is typically conducted in basic conditions, the product mixture contains lactate salts. In some preferred embodiments, solution containing lactate salts is passed through a cation exchange column to produce lactic acid which is subsequently hydrogenated. While reaction with lactates and/or lactic acid has been described with regard to products of hydrogenolysis reactions, it should be appreciated that the descriptions are equally applicable to lactates or lactic acid from any source. The lactic acid hydrogenation reaction can be conducted utilizing any suitable hydrogenation catalyst, but preferably contains at least one of Ru, Pt, Pd, Ir, and Rh; and more preferably, the rhenium-containing catalysts described above.

Hydrogenation of lactic acid preferably occurs in a temperature range of 110 to 200° C., more preferably 140 to 170° C. The hydrogenation of lactic acid should be conducted under neutral or acid conditions, preferably at a pH of 1 to 6, more preferably 3 to 5.

In flow reactors, the lactic acid hydrogenation reaction is preferably conducted at a weight hourly space velocity (WHSV) of 0.3 to 3 kg reactant per kg catalyst per hour. In batch reactors, lactic acid hydrogenation reaction times preferably range from 0.3 to 10 hours.

In another aspect of the invention, glycerol is hydrogenated to PG. In some preferred embodiments, glycerol is separated (or PG and/or other hydrogenolysis products are removed) from a product mixture such as from sugar alcohol hydrogenolysis, and the resulting glycerol-enhanced (i.e., glycerol in a higher relative proportion than in the initial product mixture) composition subjected to hydrogenation in the presence of a rhenium-containing catalyst as described above. Preferred reaction conditions are the same as those described for sugars or sugar alcohols, although the glycerol to PG reaction can be operated over a higher temperature range while still maintaining good selectivity.

The hydrogenation/hydrogenolysis reactions can occur in any reactor suitable for use under the desired conditions of temperature, pressure, and solvent. Examples of suitable apparatus include: trickle bed, bubble column reactors, and continuous stirred tank. Various additional components such as cation exchange columns, distillation columns, etc. are known to skilled workers and can be used in various embodiments of the present invention.

The inventive compositions and catalytic methods can also be characterized by their properties. Preferably, sugars and sugar alcohols are greater than 50% converted, more preferably greater than 80% converted, and still more preferably greater than 90% converted. Preferably, these conversion rates co-occur with other characteristics of the inventive compositions and catalytic methods. Preferred carbon molar selectivity ("selectivity") of sugar or sugar alcohols to PG is at least 20%, more preferably at least 30%, and in some embodiments in the range of 25 to about 40%. Selectivity of sugar or sugar alcohols to glycerol is at least 20%, more preferably at least 25%, and in some embodiments in the range of 20 to about 32%. Selectivity of the sum of PG, EG and glycerol is preferably at least 60%, more preferably at least 75%, and in some embodiments in the range of 70 to about 90%.

Various embodiments of the present invention are characterized by numerous surprisingly superior results including: enhanced selectivity to PG from sugar alcohols or glycerol; better PG yield from lactic acid with high hydrogen pressure; and enhanced PG yield by converting lactate to lactic acid.

EXAMPLES

Preparation Of Nickel/Rhenium on Carbon Catalyst

The carbon used for this preparation was a Calgon 120% CTC coconut carbon. Incipient wetness for the carbon was measured at 0.85 cc of liquid per gram of carbon. Moisture content was determined to be 1.3%.

The impregnation volume was calculated using the incipient wetness of 0.85 cc/g. The total weight of catalytic metal required is calculated by the following formula:

$$W_{mtl} = W_C * ((1/P_C) - 1)$$

Where $W_C$ is the weight of carbon being impregnated and $P_C$ is the weight percent of carbon in the reduced catalyst mix, calculated by taking 1 minus the weight percent of catalytic metal desired. In the case of 2.5 wt % nickel/2.5 wt % rhenium catalyst the $P_C$ value is 0.95.

The weight of each of the catalytic metals ($W_{Ni}$ and $W_{Re}$) is determined by multiplying the total weight of catalytic metal by the fraction that each particular metal represents in the total catalytic metal weight. Thus:

$$W_{Ni} = W_{mtl} * (P_{Ni}/P_{Ni} + P_{Re})$$

$$W_{Re} = W_{mtl} * (P_{Re}/P_{Ni} + P_{Re})$$

Where $P_{Ni}$ and $P_{Re}$ are the weight percents of nickel and rhenium respectively in the reduced catalyst. In the case of 2.5 wt % nickel/2.5 wt % rhenium catalyst the $P_{Ni}$ and $P_{Re}$ value are both 0.025.

The nickel was added to the catalyst as nickel nitrate ($NiNO_3$) from laboratory stock chemicals. In this state, the nickel nitrate is about 20.2% nickel by weight. Thus, the weight of the nickel nitrate required ($W_{NiNo3}$) is calculated by:

$$W_{NiNO3} = W_{Ni}/0.392$$

The rhenium was added to the catalyst as perrhenic acid (HReO₄) from Alfa Aesar. In this state, perrhenic acid is about 54.5% rhenium by weight, although this can vary between 50% to 55% depending on the supplier. Thus the weight perrhenic acid needed ($W_{HReO_4}$) is calculated by:

$$W_{HReO_4} = W_{Re}/0.545$$

Approximately 1.5 times the weight of water was added to the nickel nitrate in order to dissolve the material. This is approximate, and designed just to dissolve the nickel nitrate. To this mixture, the calculated amount of perrhenic acid was added to the solution. The solution was added dropwise to the carbon adding about 10% of the solution at a time. Between additions, the carbon is shaken thoroughly. Care should be taken to add the solution slowly, as the first additions to the bare carbon heat up very quickly and may boil on the surface of the carbon.

After the entirety of the impregnation solution has been added, the vessel should be capped and let sit (with intermittent shaking) for a minimum of 15 minutes for smaller batches (5 g) and at least 30 minutes for larger batches. After sitting, the vessel was placed uncapped into a vacuum oven and heated to 80 C and held at about 20 inHg (510 mmHg) vacuum. The catalyst should be held at these conditions for 18 hours, or until dry.

Upon removing the vessel from the vacuum oven, it was capped and allowed to cool. The catalyst was reduced before using.

Glycerol and Sorbitol Testing Examples
Glycerol Batch Reactor 16.57 g of Calgon 120% CTC Coconut Carbon (16×40 mesh) were placed into a jar. This carbon was determined to have an incipient wetness value of approximately 0.9 cc/g for uptake of water. In a graduated cylinder, 4.57 g of nickel nitrate was measured. To this cylinder, 1.71 g of perrhenic acid was added and then topped up to 15.0 ml with deionized water. The mixture was then allowed to sit for about 5 minutes. The solution was then added to the weighed carbon by pipette in 1 ml increments. After each 1 ml aliquot, the carbon jar was capped, shaken, and thoroughly mixed. Upon addition of the entire 15.0 ml of solution, the carbon was sticky and slightly clumped, partially adhering to the inside of the jar. The loaded carbon was allowed to sit for 20 minutes, with intermittent shaking. The jar was placed, uncapped, in a vacuum oven set to 100° C. and −20 inHg and left to dry overnight. The jar was then capped and cooled.

2.5 g of the dried catalyst was then loaded into a 300 cc semi-batch Parr reactor, which was then purged with nitrogen at room temperature. The reactor was filled to 500 psi (3.45 MPa) of hydrogen. The reactor was slowly stirred and brought up to 280° C. and held for 16 hours. The reactor was then cooled, the gas removed, and 106.1 g of a solution of 25% glycerol and 0.5% sodium hydroxide in water added. 600 psi (4.14 MPa) of hydrogen was put into the reactor and the heat turned on. After 19 minutes, when the reactor reached 230° C., the pressure was raised to 1300 psi (8.9 MPa) by adding hydrogen and held at an average pressure of 1200 psi (8.2 MPa) by adding hydrogen to the reactor to raise it to 1300 psi (9.0 MPa) whenever it dipped to 1100 psi (7.6 MPa). The test was held at temperature for 4 hours and samples were pushed out intermittently through a valved dip tube.

HPLC analysis of the products is shown in the following tables. All selectivity data is shown in carbon molar selectivity. The prefix "Eng" means that the catalyst support was obtained from Engelhard, and the suffix, such as "95" refers to the CTC value of the support provided by the manufacturer.

TABLE 1

Batch Glycerol Hydrogenation as a Function of Time at 230° C.

| hour | Conversion | Selectivity To | | |
|---|---|---|---|---|
| | | PG | EG | Lactate |
| 1 | 25.3 | 72.3 | 16.4 | 14.8 |
| 2 | 37.2 | 64.8 | 15.0 | 10.3 |
| 4 | 62.4 | 66.3 | 13.4 | 5.1 |

Figure 1:
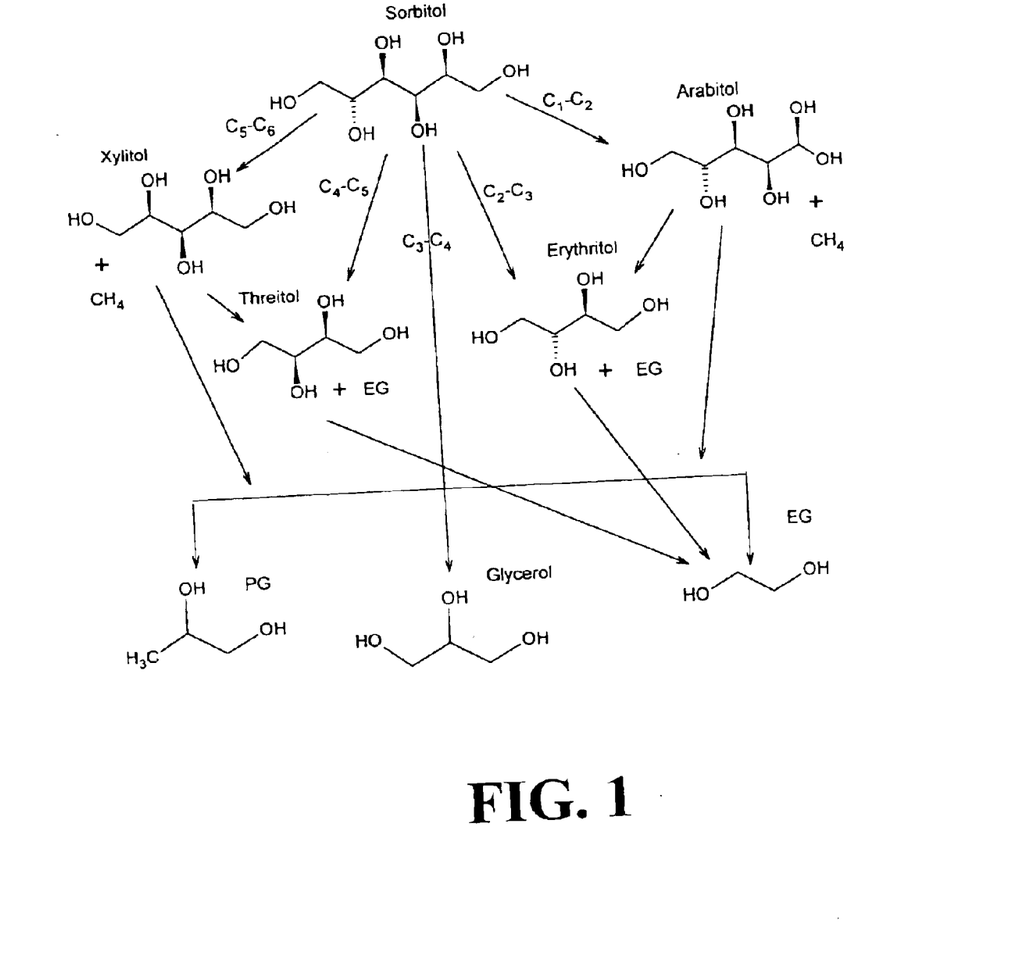
FIG. 1 illustrates various pathways for the hydrogenolysis of sorbitol and related compounds.
Figure 2:
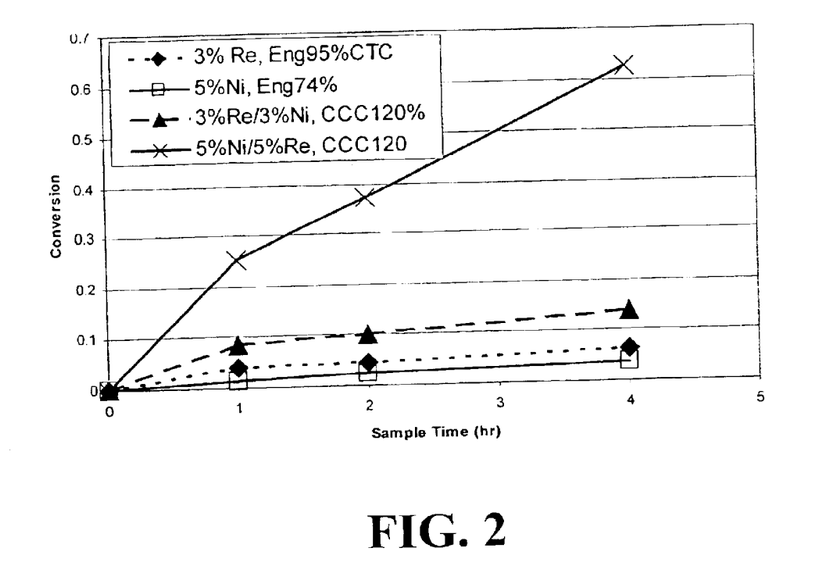
FIG. 2 is a plot of conversion vs. reaction time for glycerol hydrogenation over four catalysts.
Figure 3:
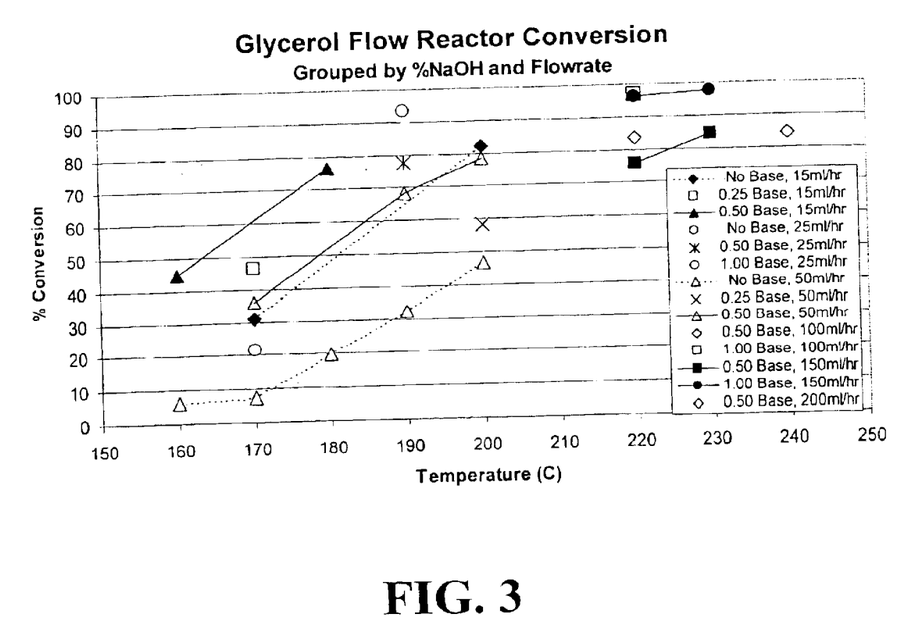
FIG. 3 is a plot of conversion vs. reaction temperature for glycerol hydrogenation over a Ni/Re catalyst at varying pH and flowrate.

Conversion and selectivity over four different catalysts as a function of time is shown in FIGS. 2 and 3.

TABLE 2

Glycerol Batch Hydrogenation - Conversion and Selectivity at 4 Hr, 230° C.

| 4 hr sample, 230 C | | Ni/Re | Re/Ni | Ni | Re | Pressure | | Carbon Molar Selectivity To: | | |
|---|---|---|---|---|---|---|---|---|---|---|
| Run | Catalyst | ratio | ratio | wt % | wt % | MPa | Conv. | Lactate | EG | PG |
| Gly-54 | 2% Ni/0.4% Re | 5.0 | 0.2 | 2 | 0.4 | 4.14 | 36 | 19 | 12 | 42 |
| Gly-46 | 2% Ni/0.4% Re | 5.0 | 0.2 | 2 | 0.4 | 4.14 | 39 | 16 | 9 | 60 |
| Gly-45 | 2% Ni/0.4% Re | 5.0 | 0.2 | 2 | 0.4 | 12.41 | 61 | 8 | 9 | 88 |
| Gly-55 | 2% Ni/0.4% Re | 5.0 | 0.2 | 2 | 0.4 | 12.41 | 60 | 10 | 13 | 78 |
| Gly-48 | 2% Ni/0.67% Re | 3.0 | 0.34 | 2 | 0.67 | 8.27 | 51 | 12 | 12 | 76 |
| Gly-43 | 2% Ni/1.33% Re | 1.5 | 0.67 | 2 | 1.33 | 4.14 | 58 | 9 | 10 | 58 |
| Gly-44 | 2% Ni/1.33% Re | 1.5 | 0.67 | 2 | 1.33 | 12.41 | 50 | 13 | 12 | 68 |
| Gly-39 | 5% Ni/1% Re | 5.0 | 0.2 | 5 | 1 | 8.27 | 50 | 10 | 11 | 67 |
| Gly-40 | 5% Ni/1% Re | 5.0 | 0.2 | 5 | 1 | 8.27 | 44 | 9 | 9 | 64 |
| Gly-50 | 5% Ni/1.67% Re | 3.0 | 0.33 | 5 | 1.67 | 12.41 | 53 | 13 | 13 | 76 |
| Gly-47 | 5% Ni/3.33% Re | 1.5 | 0.67 | 5 | 3.33 | 4.14 | 68 | 9 | 18 | 53 |
| Gly-51 | 7% Ni/1% Re | 7.0 | 0.14 | 7 | 1 | 4.14 | 49 | 16 | 12 | 62 |
| Gly-38 | 7% Ni/1% Re | 7.0 | 0.14 | 7 | 1 | 8.27 | 48 | 9 | 9 | 64 |
| Gly-49 | 7% Ni/1% Re | 7.0 | 0.14 | 7 | 1 | 12.41 | 53 | 10 | 11 | 79 |
| Gly-56 | 7% Ni/1% Re | 7.0 | 0.14 | 7 | 1 | 12.41 | 56 | 12 | 13 | 75 |
| Gly-41 | 7% Ni/1.4% Re | 5.0 | 0.2 | 7 | 1.4 | 4.14 | 70 | 8 | 10 | 54 |
| Gly-36 | 7% Ni/1.4% Re | 5.0 | 0.2 | 7 | 1.4 | 8.27 | 48 | 11 | 12 | 63 |
| Gly-42 | 7% Ni/1.4% Re | 5.0 | 0.2 | 7 | 1.4 | 12.41 | 45 | 11 | 12 | 58 |
| Gly-57 | 7% Ni/1.4% Re | 5.0 | 0.2 | 7 | 1.4 | 12.41 | 55 | 12 | 13 | 68 |
| Gly-37 | 7% Ni/2.25% Re | 3.1 | 0.32 | 7 | 2.25 | 8.27 | 55 | 9 | 13 | 60 |

TABLE 3

Glycerol Batch Hydrogenation Over Various Catalysts

| Glycerol Hydrogenolysis Catalyst | At 4 Hours Conv | PG Sel | Lactic Sel | EG Sel | Temp (C.) | Base (%) | glass liner |
|---|---|---|---|---|---|---|---|
| 3% Ag, Eng95 | 10.2 | 39.3 | 31.2 | 7.0 | 250 | 4.1 | yes |
| 3% Re, Eng95 | 6.3 | 48.3 | 10.4 | 3.8 | 200 | 4.1 | yes |
| 1.5% Cu/1.5% Re, CCC120 | 9.5 | 45.9 | 5.3 | 4.5 | 200 | 4.1 | yes |
| 1.5% Ag/1.5% Re, CCC120 | 5.9 | 49.5 | 8.5 | 4.1 | 200 | 4.1 | yes |
| 5% Ni/5% Re, Eng121 | 41.2 | 63.2 | 20.1 | 9.3 | 200 | 4.1 | yes |
| 1.5% Ag/1.5% Re, CCC120 | 8.0 | 59.2 | 14.0 | 5.5 | 200 | 4.1 | no |
| 5% Ni, Eng74 | 2.6 | 88.5 | 11.1 | 4.6 | 200 | 1 | no |
| 3% Ni/3% Cu, CCC120 | 7.0 | 84.0 | 10.8 | 6.1 | 200 | 1 | no |
| 3% Cu/3% Re, CCC120 | 12.3 | 76.6 | 8.5 | 2.0 | 200 | 1 | no |
| 3% Ni/3% Re, CCC120 | 13.8 | 63.8 | 15.1 | 14.9 | 200 | 1 | no |
| 9% Rh/9% Re, Eng121 | 14.7 | 70.1 | 2.7 | 14.4 | 150 | 1 | no |
| 3% Ni/3% Re, CCC120 | 25.8 | 66.9 | 13.5 | 11.2 | 200 | 2 | no |

TABLE 4

Glycerol Batch Hydrogenation Over Various Catalysts

| Glycerol Hydrogenolysis Catalyst | Conv. | PG | 1,3-PD | Lactic | EG | Temp | Base (%) |
|---|---|---|---|---|---|---|---|
| 5% Ni/5% Re, CCC120 | 62.4 | 66.3 | 0.0 | 5.1 | 13.4 | 230 | 2 |
| 5% Ni/5% Re, Eng95 | 49.7 | 58.9 | 0.0 | 7.8 | 15.1 | 230 | 2 |
| 2.5% Pd/5% Re, Eng95 | 49.1 | 50.6 | 0.0 | 7.4 | 5.1 | 230 | 2 |
| 5% Pd/5% Re, Eng95 | 48.9 | 55.2 | 0.0 | 7.2 | 6.0 | 230 | 2 |
| 2.5% Ni/2.5% Re, CCC120 | 47.3 | 44.3 | 4.6 | 0.0 | 13.0 | 230 | 0 |
| 5% Ni/5% Re, Eng95 | 47.1 | 52.7 | 0.0 | 3.2 | 17.6 | 230 | 1 |
| 5% Ni/5% Re, Eng95 | 46.9 | 53.3 | 0.0 | 0.4 | 19.5 | 230 | 0 |
| 5% Pd/5% Re, Eng95 | 41.0 | 48.3 | 0.0 | 4.2 | 5.4 | 230 | 1 |
| 5% Pd/5% Re, Eng95 | 38.9 | 46.8 | 0.0 | 0.4 | 5.4 | 230 | 0 |
| 2.5% Ni/2.5% Re, Eng95 | 38.4 | 54.0 | 2.4 | 2.0 | 14.3 | 230 | 0 |
| 2.5% Pd/2.5% Re, CCC120 | 25.5 | 50.6 | 5.2 | 0.0 | 5.8 | 230 | 0 |
| 5% Ni, Eng95 | 15.7 | 56.0 | 0.0 | 19.2 | 6.1 | 230 | 2 |
| 5% Re, Eng95 | 13.7 | 40.2 | 0.0 | 20.6 | 4.2 | 230 | 2 |

There were many unexpected results from the glycerol hydrogenolysis. As can be seen from the data, the selectivity to lactate decreases substantially with increasing time. Conversion and selectivity depend on both the type of catalyst and hydrogen pressure. Re-containing multimetallic catalysts resulted in substantially better PG selectivity and conversion. The performance of the Ni—Re catalysts was especially good. Increased hydrogen pressure was unexpectedly discovered to result in enhanced PG selectivity. Also, where base was not added to the glycerol feedstock, 1,3-propanediol was unexpectedly found to be produced from the hydrogenolysis of glycerol.

In some preferred embodiments, the conversion of glycerol to PG is conducted as a separate step from the hydrogenolysis of a sugar alcohol. In this two step (or multi-step) process, glycerol resulting from the hydrogenolysis of a sugar alcohol is isolated or its relative concentration increased (for example by removing at least a portion of the PG, or other product, produced). In some preferred embodiments, glycerol is present at a higher concentration than the sum of PG, EG and sugar alcohol.

Glycerol Flow Reactor Example 13.37 g of 120% CTC Calgon Coconut Carbon ("CCC," 16×40 Mesh) was placed into a jar. To a graduated cylinder containing 1.7402 of Nickel Nitrate was added 0.6974 g of perrhenic acid and then topped up to 11.5 ml with deionized water. This solution was then added to the weighed carbon by pipette in 1.0 ml increments. After each 1.0 ml aliquot, the carbon was shaken, and thoroughly mixed. Upon addition of the entire 11.5 ml of solution, the carbon was sticky and slightly clumped, partially adhering to the inside of the jar. The loaded carbon was allowed to sit for 45 minutes, with intermittent shaking. The carbon appeared mostly dry and granular, with some material still adhering to the inside of the jar. The jar was placed, uncapped, in a vacuum oven set to 100° C. and −20 inHg and left to dry overnight. The jar was then capped and cooled. The catalyst was designated as a 2.5% nickel/2.5% rhenium catalyst.

11.41 g of this dried catalyst was placed in a downflow trickle-bed reactor and packed to constitute a 30 cc bed. Hydrogen was passed slowly across the bed at atmospheric pressure, and the bed was heated to 120° C. and held for 18 hours. The temperature was raised to 280° C. and held for 4 hours. The reactor was then cooled under hydrogen.

The reactor was then raised to 1200 psi and 160° C., and a large set of reaction conditions were tested for converting a glycerol feedstock to propylene glycol. This was accomplished by processing a 10% glycerol (by weight) feedstock at a hydrogen excess of 5 to 1 at full reaction, while varying temperatures from 160° C. to 240° C., pressures between 800 psi and 1600 psi, base concentrations between 0 and 1% (by weight of feedstock), and flowrates between 15 and 200 ml/hr.

Figure 4:
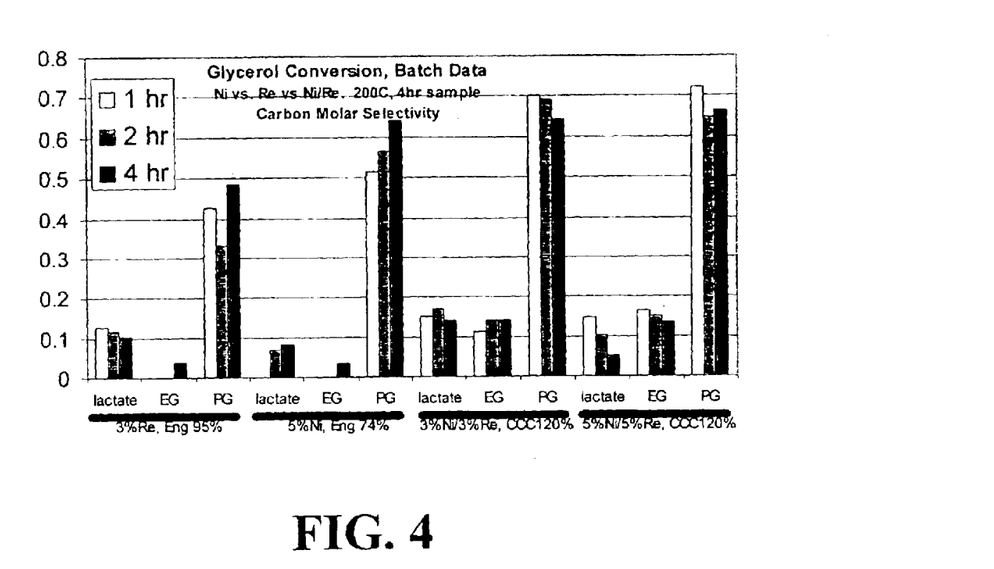
FIG. 4 is a plot of selectivity for glycerol hydrogenation over four catalysts at various reaction times.
Figure 5:
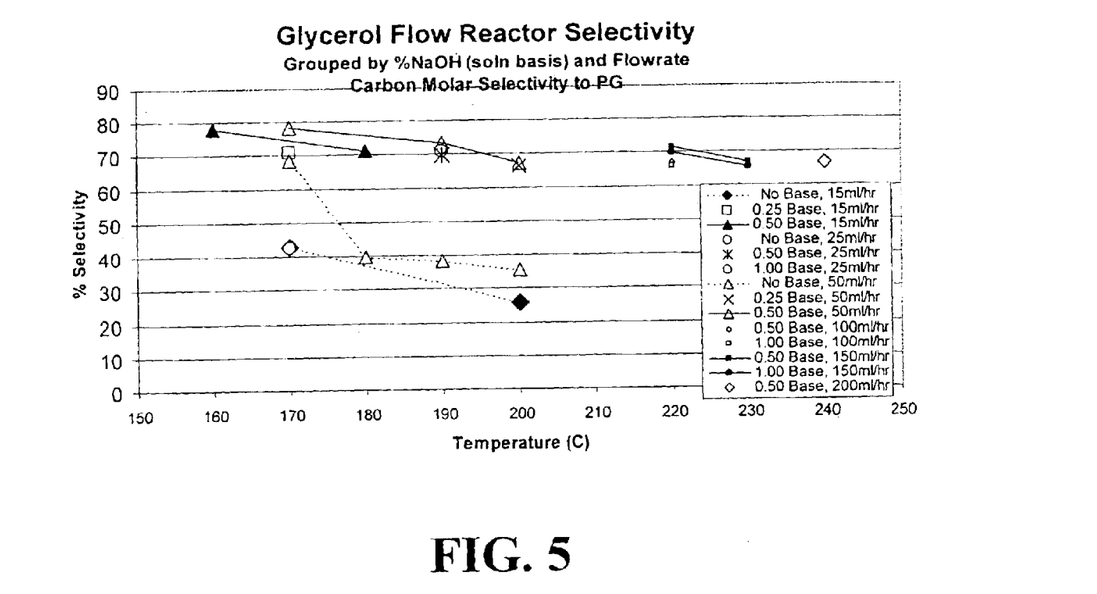
FIG. 5 is a plot of selectivity vs. temperature for glycerol hydrogenation over a Ni/Re catalyst at varying pH and flowrate.

Selected data for the glycerol hydrogenation over a 2.5% Ni/2.5% Re/C catalyst in a flow reactor is summarized in FIGS. 4 and 5. The amount of NaOH is indicated in units of wt % NaOH in the solution. The presence of base was unexpectedly found to substantially increase the conversion rate and selectivity to PG. The reasons for effect is not known, but it could be that base enhances the wetting of catalyst. In preferred embodiments, the molar ratio of base/ glycerol is at least 0.05, more preferably in the range of 0.1 to 1.0, and still more preferably 0.1 to 0.5; or, in another preferred embodiment, the solution is between 0.25 and 5 weight % base. Preferably, the reaction is run at a pressure in the range of 600 to 1800 psi (4 to 12 MPa) hydrogen. Temperature of the glycerol hydrogenation is preferably in the range of 170 to 250° C., more preferably 200 to 230° C. Glycerol conversion is preferably at least 80%, more preferably at least 90%, and in some embodiments 80–97%. PG selectivity is preferably at least 50%, more preferably at least 60%, and in some embodiments 60 to about 80%.

Sorbitol Flow Reactor Examples

These examples used the same bed as was used for the glycerol flow reactor testing. Following the glycerol conversion testing, the reactor was used to examine the conversion of sorbitol over the Ni/Re catalyst. The reactor was heated and pressurized with hydrogen to 1200 psi (8.3 MPa) and 200° C., and a number of reaction conditions were tested for converting the sorbitol feedstock to PG, EG, and glycerol. This was accomplished by processing a 25% sorbitol (by weight) feedstock at a hydrogen excess of 5 to 1 at full reaction, while varying the temperatures between 180° C. and 240° C., pressures between 1200 psi (8.3 MPa) and 1800 psi (12.4 MPa), base concentrations between 0.5 and 1.5% (by weight), and flowrates between 15 and 75 ml/hr. The run was compared against a previous flow reactor experiment using a 2.5% ruthenium catalyst and equivalent flowrate and bed volume combination. A portion of the results are summarized in the FIGS. 6–8.

Figure 6:
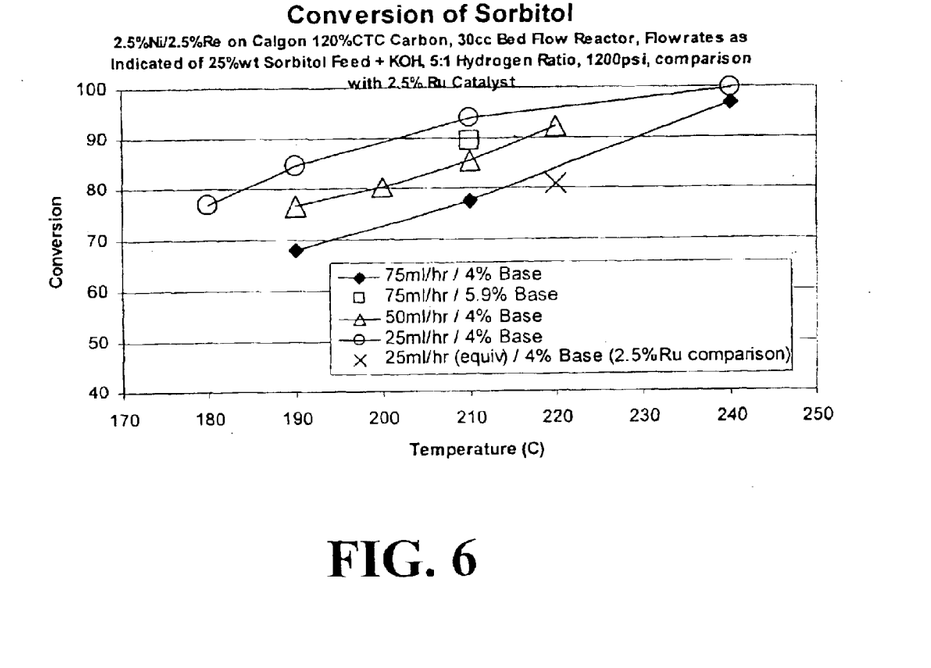
FIG. 6 is a plot of conversion vs. temperature for sorbitol hydrogenolysis over a Ni/Re catalyst at varying pH and flowrate, and a comparison with a Ru catalyst.
Figure 7:
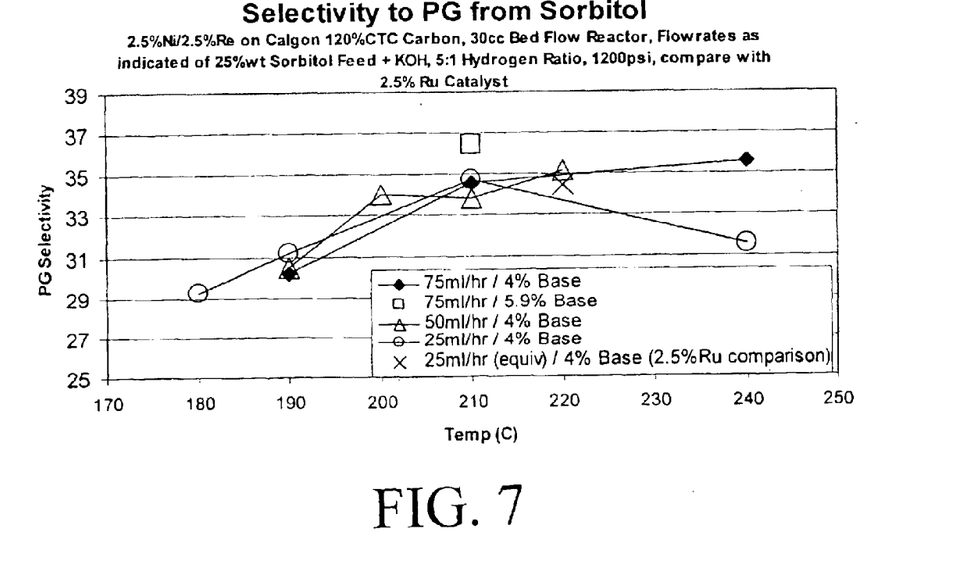
FIG. 7 is a plot of PG selectivity vs. temperature for sorbitol hydrogenolysis over a Ni/Re catalyst at varying pH and flowrate, and a comparison with a Ru catalyst.
Figure 8:
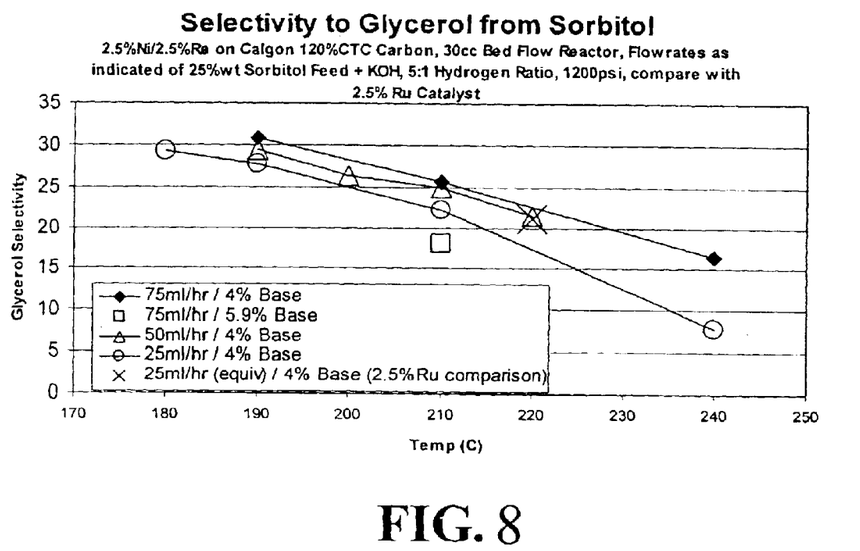
FIG. 8 is a plot of glycerol selectivity vs. temperature for sorbitol hydrogenolysis over a Ni/Re catalyst at varying pH and flowrate, and a comparison with a Ru catalyst.

From the data it can be observed that the Ni/Re catalyst exhibited good selectivity to PG while at the same time providing superior conversion rates as compared to a Ru catalyst.

Sorbitol Batch Reactor Example 5.09 g of Calgon 120% CTC Coconut Carbon was placed into a jar. To a graduated cylinder containing 0.6728 of Nickel Nitrate was added 0.2525 g of perrhenic acid and then topped up to 4.4 ml with deionized water. The mixture was then allowed to sit for about 5 minutes. The solution was then added to the weighed carbon by pipette in 0.5 ml increments. After each 0.5 ml aliquot, the carbon was shaken, and thoroughly mixed. Upon addition of the entire 4.4 ml of solution, the carbon was sticky and slightly clumped, partially adhering to the inside of the jar. The loaded carbon was allowed to sit for 30 minutes, with intermittent shaking. The carbon appeared mostly dry and granular, with some material still adhering to the inside of the jar. The jar was placed, uncapped, in a vacuum oven set to 100° C. and −20 inHg (510 mmHg) and left to dry overnight. The jar was then capped and cooled.

2.53 g of the dried catalyst were then loaded into a 300 cc semi-batch Parr reactor, which was then purged with nitrogen at room temperature. The reactor was filled with 3.5 MPa (500 psi) of hydrogen. The reactor was slowly stirred and brought up to 280° C. and held for 16 hours. The reactor was then cooled, the gas removed, and 105.5 g of a solution of 25% sorbitol and 0.94% potassium hydroxide in water was added. 600 psi (4.1 MPa) hydrogen was put into the reactor and the heat was turned on. After 20 minutes, when the reactor reached 220° C., the pressure was raised to 1200 psi (8.3 MPa) by adding hydrogen and the hydrogen intake valve was left open regulated to 1200 psi (8.3 MPa). The test was held at temperature for 4 hours and samples were pushed out intermittently through a valved dip tube.

Samples were analyzed via HPLC to yield the results shown in the tables below. The 0.0 hour value corresponds to the point at which the reactor reached operating temperature. Batch data in the tables was collected in samples containing 0.94 wt. % KOH. As can be seen, selectivity to glycerol decreased with increasing reaction time due to continuing C—O hydrogenolysis. Although there appears to be variations in the data, in general, it appears that improved hydrogen pressure causes increased conversion.

TABLE 5

Batch Sorbitol Hydrogenolysis as a Function of Time

| hr | Conv. | xylitol | erythritol | unk-OH | lactate | glycerol | 1,2,4BTO | EG | PG | 2,3 BDO | 1,3 BDO | 1,2 BDO |
|---|---|---|---|---|---|---|---|---|---|---|---|---|
| 0.0 | 17.1 | 5.1 | 1.8 | 3.2 | 5.2 | 22.9 | 0.0 | 13.2 | 29.4 | 3.7 | 0.0 | 2.5 |
| 1.0 | 37.9 | 8.3 | 3.2 | 3.6 | 6.9 | 20.2 | 1.6 | 10.7 | 18.8 | 1.9 | 0.0 | 1.4 |
| 2.0 | 42.6 | 10.7 | 3.6 | 4.0 | 8.1 | 21.5 | 2.2 | 11.4 | 20.8 | 1.5 | 0.8 | 1.5 |
| 4.0 | 56.3 | 9.6 | 2.7 | 2.9 | 5.6 | 17.4 | 2.3 | 10.1 | 20.9 | 2.4 | 0.0 | 2.5 |

TABLE 6

Batch Sorbitol Hydrogenolysis at 4 Hours at 220° C.

Sorbitol Batch Data, 4 Hour Sample, 220 C

| Run | Ni wt % | Re wt % | Pressure MPa | Conv | Carbon Molar Selectivity to: | | | | | | |
|---|---|---|---|---|---|---|---|---|---|---|---|
| | | | | | xylitol | erythritol | threitol | lactate | glycerol | EG | PG |
| Sorb20 | 7 | 2.25 | 8.27 | 58.5 | 9 | 3 | 3 | 6 | 19 | 11 | 22 |
| Sorb25 | 7 | 1.4 | 4.14 | 62.8 | 5 | 1 | 2 | 4 | 9 | 7 | 15 |
| Sorb19 | 7 | 1.4 | 8.27 | 57.8 | 8 | 3 | 3 | 6 | 19 | 12 | 22 |
| Sorb26 | 7 | 1.4 | 12.41 | 48.8 | 7 | 2 | 3 | 6 | 16 | 10 | 19 |
| Sorb47 | 7 | 1 | 4.14 | 39.3 | 0 | 5 | 0 | 13 | 19 | 16 | 30 |
| Sorb21 | 7 | 1 | 8.27 | 51.6 | 7 | 2 | 3 | 7 | 19 | 13 | 23 |
| Sorb45 | 7 | 1 | 12.41 | 57.0 | 7 | 3 | 4 | 9 | 29 | 16 | 27 |
| Sorb46 | 5 | 3.33 | 4.14 | 56.8 | 8 | 5 | 0 | 9 | 17 | 13 | 24 |
| Sorb48 | 5 | 1.67 | 12.41 | 58.8 | 8 | 3 | 4 | 10 | 26 | 15 | 24 |
| Sorb22 | 5 | 1 | 8.27 | 55.3 | 7 | 3 | 3 | 6 | 20 | 12 | 23 |

TABLE 6-continued

Batch Sorbitol Hydrogenolysis at 4 Hours at 220° C.

Sorbitol Batch Data, 4 Hour Sample, 220 C

| Run | Ni wt % | Re wt % | Pressure MPa | Conv | Carbon Molar Selectivity to: | | | | | | |
|---|---|---|---|---|---|---|---|---|---|---|---|
| | | | | | xylitol | erythritol | threitol | lactate | glycerol | EG | PG |
| Sorb27 | 2 | 1.33 | 4.14 | 54.2 | 7 | 2 | 2 | 6 | 12 | 10 | 21 |
| Sorb44 | 2 | 1.33 | 12.41 | 57.4 | 8 | 3 | 4 | 10 | 27 | 15 | 25 |
| Sorb32 | 2 | 0.67 | 8.27 | 54.5 | 6 | 2 | 3 | 8 | 19 | 13 | 24 |
| Sorb34 | 2 | 0.4 | 4.14 | 44.2 | 7 | 2 | 3 | 10 | 15 | 14 | 29 |
| Sorb35 | 2 | 0.4 | 12.41 | 55.7 | 4 | 2 | 2 | 5 | 20 | 15 | 31 |

Xylitol Flow Reactor Examples

The catalyst used for these examples was a 2.5% Ni/2.5% Re on 120% CTC CCC support, prepared as described above. The flow reactor was operated as discussed above with a xylitol feed concentration of 20 wt. % and a hydrogen pressure of 12.4 MPa (1200 psi). Base % is the wt % of KOH present in the feedstock.

Xylitol flow and batch data is reported in terms of weight % selectivity which is defined as the weight of a particular product compound recovered (such as PG produced in this case) divided by the weight of the feedstock compound actually converted (such as xylitol converted in this case). For example, if 100 grams of xylitol was fed into a reactor as the feedstock, and 50 g of xylitol was converted to 30 g of PG and 20 g of EG, then the weight % selectivity for PG would be 30 g/50 g or 60 weight % selectivity. Likewise, the weight % selectivity for the EG product would be 20 g/50 g or 40 weight % selectivity.

selectivity to PG. PG yield could be increased further by acidifying the lactate by-product to lactic acid followed by hydrogenation to convert the lactic acid to PG.

Xylitol Batch Hydrogenolysis

Figure 9:
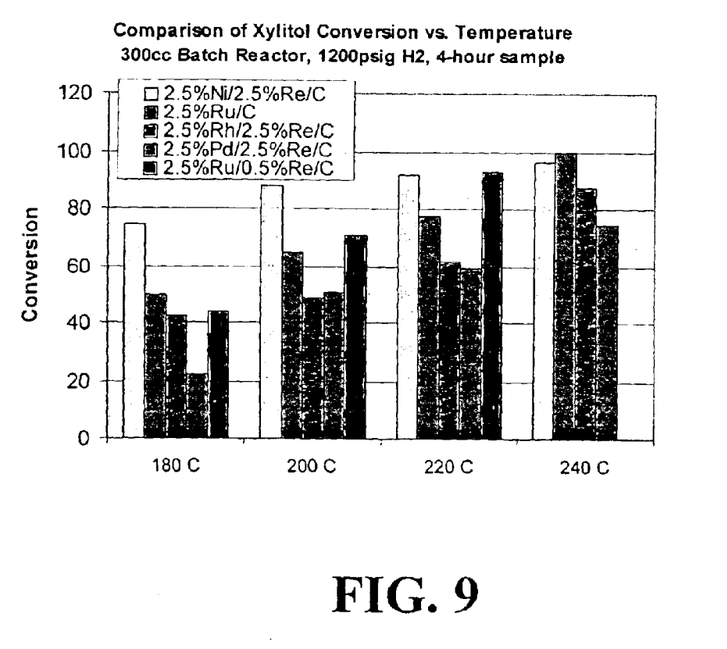
FIG. 9 is a plot of conversion vs. temperature for xylitol hydrogenolysis over four catalysts.
Figure 10:
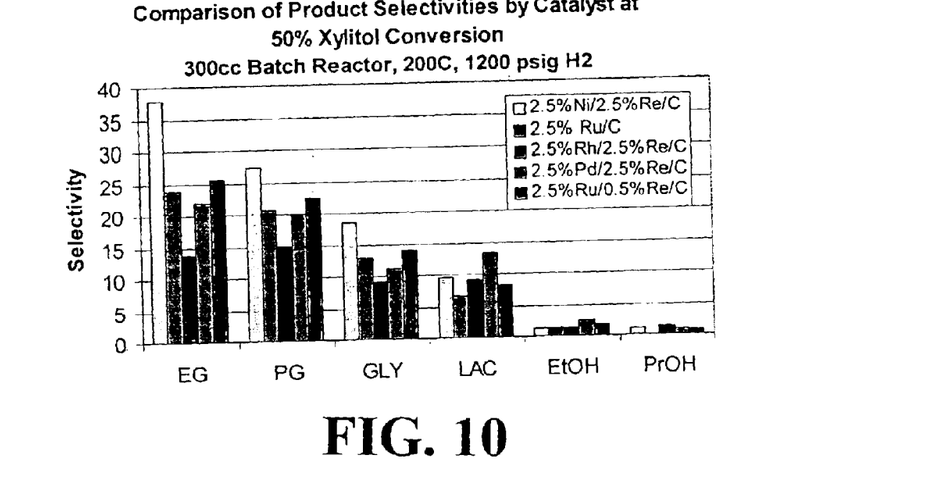
FIG. 10 is a plot of selectivities vs. temperature for xylitol hydrogenolysis over five catalysts at 200° C.

Xylitol batch hydrogenolysis was conducted under conditions as described above for sorbitol. Results are shown in FIGS. 9 and 10. Xylitol conversion was measured at 4 hours over the catalysts (left to right in FIG. 9) 2.5 wt. % Ni/2.5 wt. % Re/C, 2.5% Ru/C, 2.5% Rh/2.5% Re/C, 2.5% Pd/2.5% Re/C, and 2.5% Ru/0.5% Re/C. The Ni/Re catalyst resulted in surprisingly superior conversion. Furthermore, the Ni/Re catalyst demonstrated surprisingly superior selectivity to PG, EG and glycerol.

Arabinitol Batch Hydrogenolysis

TABLE 7

Xylitol Flow Reactor Summary

| Temp (C.) | 140 | 160 | 160 | 160 | 160 | 160 | 170 | 170 | 180 | 180 | 180 | 200 | 200 | 200 | 200 |
|---|---|---|---|---|---|---|---|---|---|---|---|---|---|---|---|
| feed rate (ml/mn) | 25 | 100 | 100 | 50 | 50 | 50 | 50 | 25 | 100 | 50 | 25 | 200 | 150 | 100 | 50 |
| Contact (hr) | 1.4 | 0.35 | 0.35 | 0.7 | 0.7 | 0.7 | 0.7 | 1.4 | 0.35 | 0.7 | 1.4 | 0.175 | 0.233 | 0.35 | 0.7 |
| Base % | 1 | 1 | 0.25 | 1 | 0.25 | 0.1 | 1 | 1 | 1 | 1 | 1 | 1 | 1 | 1 | 1 |
| Conversion | 19.7 | 27.2 | 8.1 | 44.9 | 15.2 | 10.2 | 74.5 | 92.7 | 79.7 | 94.5 | 98.4 | 85.1 | 93.7 | 99.8 | 98.3 |
| Weight Selectivity | | | | | | | | | | | | | | | |
| PG | 10.2 | 13.5 | 8.5 | 16.8 | 8.8 | 6.7 | 21.9 | 26.1 | 25.9 | 28.1 | 30.3 | 29.8 | 30.8 | 29.5 | 30.8 |
| Glycerol | 22.3 | 21.0 | 22.5 | 23.2 | 21.6 | 20.2 | 16.9 | 13.6 | 17.1 | 11.3 | 8.6 | 9.7 | 8.2 | 8.7 | 7.4 |
| EG | 24.5 | 27.3 | 21.3 | 26.7 | 23.3 | 19.8 | 28.0 | 28.2 | 27.8 | 29.2 | 28.6 | 35.2 | 29.7 | 29.2 | 27.9 |
| Lactate | 32.7 | 24.5 | 37.1 | 20.9 | 33.8 | 35.2 | 11.0 | 6.4 | 8.4 | 5.0 | 3.5 | 4.3 | 3.8 | 3.9 | 3.7 |
| Other | 3.0 | 2.0 | 4.9 | 5.2 | 0.7 | 1.9 | 8.1 | 11.5 | 22.6 | 11.3 | 13.4 | 11.1 | 11.7 | 15.7 | 10.3 |

From this data can be seen the surprising results that, over a Re-containing catalyst, higher temperature, basic conditions and longer contact times improve conversion and Arabinitol was subjected to hydrogenolysis under conditions similar to the xylitol batch hydrolysis. Results are shown in Table 8 below in weight % selectivities.

| Sample # | Arabitol Conversion | EG Wt. % Selectivity | PG Wt. % Selectivity | Gly Wt. % Selectivity | Lac Wt. % Selectivity | EtOH Wt. % Selectivity | Other Wt. % Selectivity | EG + PG + Gly Selectivity |
|---|---|---|---|---|---|---|---|---|
| 0.5 Hour | 55.90% | 31.87% | 20.61% | 14.97% | 12.05% | 0.00% | 3.30% | 67.45% |
| 1.0 Hour | 75.00% | 31.44% | 20.27% | 14.52% | 11.54% | 0.00% | 2.96% | 66.23% |
| 2.0 Hour | 82.00% | 31.24% | 20.29% | 13.82% | 11.68% | 0.00% | 2.73% | 65.35% |
| 3.0 Hour | 83.90% | 31.15% | 20.43% | 13.16% | 11.45% | 0.00% | 2.69% | 64.74% |
| 4.0 Hour | 86.30% | 31.07% | 20.58% | 12.82% | 11.23% | 0.00% | 2.66% | 64.47% |

Lactic Acid Hydrogenation

Lactic Acid Batch Hydrogenation

Catalyst testing was conducted in a semi-batch mode under constant hydrogen pressure using a 300 cc, 316 SS Parr autoclave reactor system fitted with a Magnadrive stirrer and stirrer tachometer. 2.50 g of the 55794-107 pre-reduced catalyst sample was weighed into a clean Pyrex glass liner, then the liner and the contained catalyst were sealed inside the autoclave body. After pressure testing the assembled reactor system, 250 psi of pure hydrogen is charged to the reactor, the stirrer motor started and set to approximately 150 rpm then the reactor is heated up to 280° C. in order to re-reduce the catalyst prior to introduction of the feeds. The temperature is maintained at 280° C. for 4 hours, then is quickly cooled back to room temperature. After cooling, the reactor was flushed with nitrogen, then 103.8 g of a 19.7% lactate feedstock solution (19.89% lactic acid in D.I. water) was added to the reactor liner, containing the catalyst, through the liquid sampling port. The vessel was then purged several times with pure hydrogen, then re-pressurized to 1500 psi with hydrogen. The stirrer motor was turned on and the stirrer speed adjusted to ~500 rpm. The reactor was rapidly heated to 150° C. and the gas inlet opened to maintain the hydrogen pressure within the vessel at a constant 2500 psi pressure. Liquid samples are withdrawn from the vessel after 1, 2, and 4 hour intervals. The liquid samples are analyzed by high pressure liquid chromatography to determine the concentrations of residual lactic acid, PG, and propanols in the solutions. Lactic acid conversions and product selectivities for each product are then calculated. Table 9, below, shows data from the batch testing at 4 hours.

TABLE 9

Lactic Acid Hydrogenation

| Cat. Comp. | Carbon Support | Temp.(° C.) | Press.(psi) | Conv. | PG SEL. | PG Yield |
|---|---|---|---|---|---|---|
| 2.5% Pd/2.5% Zr/C | Calgon PCB | 225° C. | 1500 | 7.5% | 19.1% | 1.4% |
| 2.0% Pd/5% Zr/C | Eng. 121% CTC | 225° C. | 1500 | 4.1% | 28.3% | 1.2% |
| 2.5% Ru/10% Zr/C | Eng. 121% CTC | 200° C. | 1500 | 88.5% | 82.8% | 73.3% |
| 5% Ru/C | Calgon 120% CTC | 200° C. | 1500 | 93.7% | 66.4% | 62.2% |
| 2.5% Ru/C | Calgon PCB | 200° C. | 1500 | 76.4% | 82.8% | 63.3% |
| 2.5% Ru/10% Zr/C | Calgon 120% CTC | 200° C. | 1500 | 83.5% | 87.0% | 72.7% |
| 5% Ru/ZrO$_2$ | Eng. Zirconia | 200° C. | 1500 | 52.3% | 95.4% | 49.9% |
| 2.5% Ru/C | Calgon 120% CTC | 200° C. | 1500 | 93.3% | 74.9% | 69.8% |
| 2.5% Ru/10% Zr/C | Calgon PCB | 200° C. | 1500 | 81.3% | 76.0% | 61.8% |
| 2.5% Ru/5% Zr/C | Calgon 120% CTC | 200° C. | 1500 | 88.2% | 70.7% | 62.4% |
| 2.5% Ru/5% Zr/C | Calgon PCB | 200° C. | 1500 | 73.6% | 74.6% | 54.9% |
| 2.5% Ru/10% Zr/C | Calgon 130% CTC | 200° C. | 1700 | 89.5% | 78.7% | 70.4% |
| 2.0% Ru/C | Calgon 120% CTC | 200° C. | 1700 | 94.2% | 71.4% | 67.2% |
| 2.5% Ru/C | Calgon 120% CTC | 180° C. | 1700 | 92.9% | 83.8% | 77.8% |
| 2.5% Ru/C | Calgon 120% CTC | 180° C. | 2450 | 96.6% | 90.1% | 87.1% |
| 2.5% Ru/C | Calgon 120% CTC | 160° C. | 2450 | 86.5% | 95.2% | 82.4% |
| 2.5% Ru/C | Calgon 120% CTC | 180° C. | 2500 | 98.4% | 93.2% | 91.7% |
| 2.5% Ru/5% Zr/C | Calgon 120% CTC | 200° C. | 1600 | 92.6% | 69.7% | 64.5% |
| 2.5% Ru/15% Zr/C | Calgon 120% CTC | 180° C. | 2400 | 88.3% | 85.6% | 75.6% |
| 2.5% Ru/C | Calgon PCB | 180° C. | 2400 | 84.9% | 89.7% | 76.2% |
| 2.5% Ru/2.5% Re/C | Calgon 120% CTC | 150° C. | 2500 | 95.8% | 96.3% | 92.3% |
| 4.8% Ru/4.8% Re/C | Calgon 120% CTC | 180° C. | 2500 | 98.6% | 87.3% | 86.1% |
| 4.8% Ru/4.8% Re/C | Calgon 120% CTC | 160° C. | 2500 | 95.0% | 94.1% | 89.4% |
| 1.5% Ru/C | Calgon 120% CTC | 180° C. | 2500 | 93.9% | 93.9% | 88.1% |
| 1.5% Ru/1.5% Re/C | Calgon 120% CTC | 150° C. | 2500 | 59.5% | 100% | 59.5% |
| 1.5% Ru/1.5% Re/C | Calgon 120% CTC | 180° C. | 2500 | 99.7% | 86.0% | 85.7% |
| 1.5% Ru/1.5% Re/ | Calgon 120% CTC 5% Zr/C | 160° C. | 2500 | 72.1% | 93.8% | 67.6% |
| 1% Ru/C | Calgon 120% CTC | 180° C. | 2500 | 90.3% | 90.3% | 81.6% |
| 2.5% Ru/10% Zr/C | Calgon 120% CTC | 180° C. | 2400 | 16.1% | 100% | 16.1% |
| 1.0% Ru/5% Zr/C | Calgon 120% CTC | 180° C. | 2400 | 74.9% | 95.1% | 71.3% |
| 1.5% Ru/0.5% Re/C | Calgon 120% CTC | 160° C. | 2350 | 92.0% | 88.3% | 81.3% |
| 1.0% Ru/C | Calgon 120% CTC | 160° C. | 2350 | 70.3% | 98.7% | 69.3% |
| 1.5% Ru/C | Eng. 95% CTC | 180° C. | 2400 | 89.2% | 91.1% | 81.2% |
| 1.5% Ru/5% Zr/C | Eng. 95% CTC | 180° C. | 2400 | 88.5% | 95.2% | 84.3% |
| 1.5% Ru/5% Zr/C Zr sol prep | Calgon 120% CTC | 180° C. | 2400 | 89.4% | 88.9% | 79.5% |
| 1.5% Ru/5% Zr/C | Calgon 120% CTC | 160° C. | 2430 | 67.9% | 93.7% | 63.7% |
| 1.5% Ru/C | Calgon 120% CTC | 160° C. | 2400 | 87.0% | 91.3% | 79.5% |
| 1.5% Ru/5% Zr/C | Calgon 120% CTC | 160° C. | 2400 | 81.1% | 89.4% | 72.6% |
| 1.5% Ru/C | Calgon 120% CTC | 180° C. | 2350 | 93.6% | 88.9% | 83.2% |
| 1.5% Ru/2.5% Zr/C | Calgon 120% CTC | 180° C. | 2450 | 86.6% | 96.4% | 83.5% |
| 2.5% Ru/2.5% Re/C | Calgon 120% CTC | 180° C. | 2500 | 98.3% | 76.4% | 75.1% |
| 2.5% Ru/2.5% Zr/C | Calgon 120% CTC | 180° C. | 2500 | 95.4% | 81.6% | 77.9% |
| 1.5% Ru/1.5% Re/C | Calgon 120% CTC | 180° C. | 2500 | 99.4% | 83.4% | 82.9% |
| 4.8% Ru/4.8% Zr/C | Calgon 120% CTC | 180° C. | 2500 | 98.5% | 84.7% | 83.4% |
| 2.5% Ru/2.5% Re/C | Calgon 120% CTC | 180° C. | 2500 | 100% | 75.0% | 75.0% |
| 5% Ru/C | Calgon 120% CTC | 180° C. | 2500 | 99.4% | 77.2% | 76.7% |
| 3.5% Ru/C | Calgon 120% CTC | 180° C. | 2500 | 98.7% | 85.8% | 84.7% |
| 2.5% Ru/1.0% Zr/C | Calgon 120% CTC | 180° C. | 2500 | 96.8% | 90.5% | 87.6% |
| 3.5% Ru/1% Zr/C | Calgon 120% CTC | 180° C. | 2500 | 98.1% | 82.6% | 81.0% |
| 2.5% Ru/2.6% Ti/C | Calgon 120% CTC | 180° C. | 2500 | 94.8% | 86.7% | 82.2% |

It was surprisingly discovered that the higher hydrogen pressure improved conversion and selectivity to PG—this can be seen by comparing hydrogenation results run at 180° C. over Ru/C at 1700 psi (78% PG yield) versus 2450 psi (87% PG yield) and 2500 psi (92% PG yield). Excessive zirconia (which is coprecipitated with the metal onto the carbon support) can reduce conversion efficiency.

Figure 11:
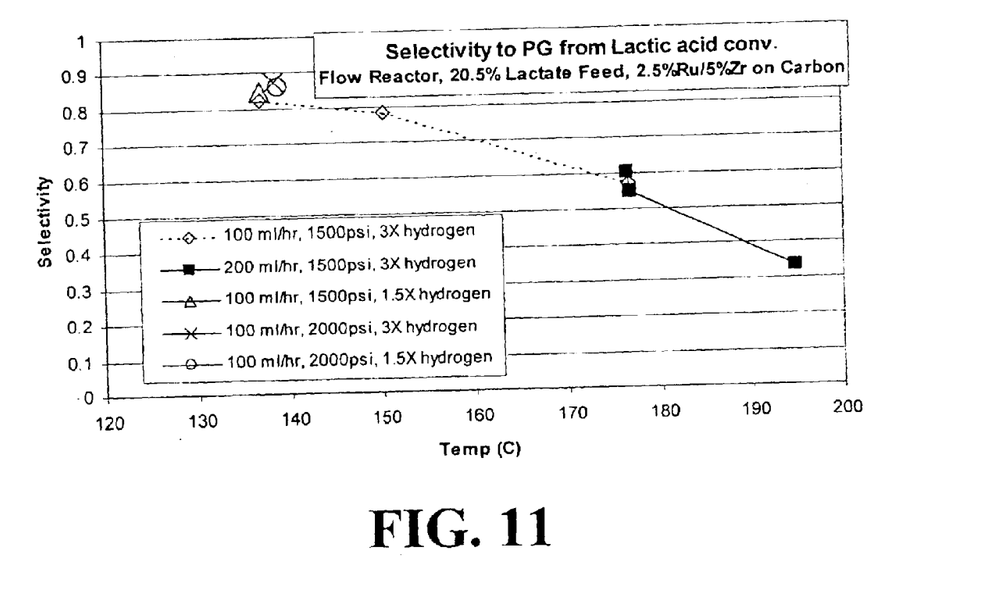
FIG. 11 is a plot of PG selectivity vs. temperature for lactic acid hydrogenation at varying pH, hydrogen pressure, hydrogen-to-lactic acid ratio, and flowrate.
Figure 12:
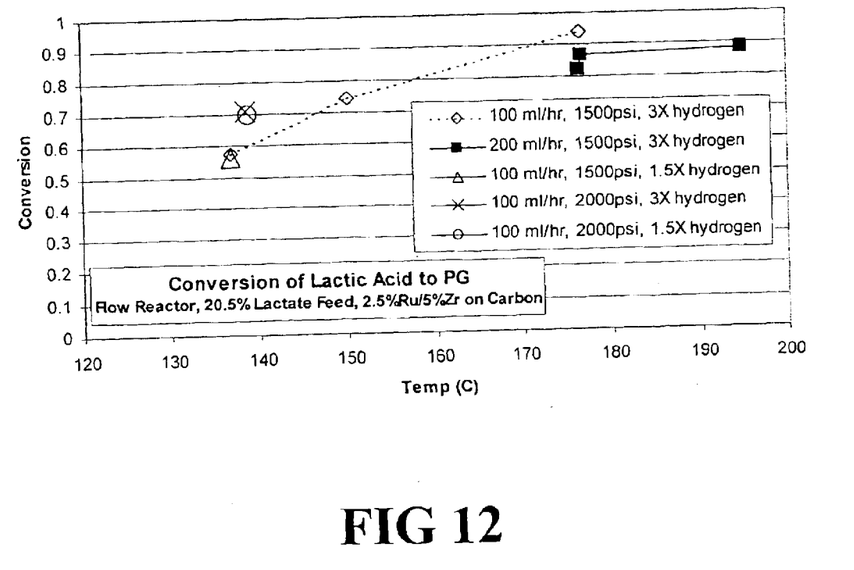
FIG. 12 is a plot of PG selectivity vs. temperature for lactic acid hydrogenation at varying pH, hydrogen pressure, hydrogen-to-lactic acid ratio, and flowrate.

Testing was also conducted in flow reactors of the conversion of lactic acid to PG. Testing conditions were similar to those described above for sorbitol except that pH was unadjusted when preparing the lactic acid feedstock resulting in an acidic solution representing the pH of lactic acid at the feedstock concentration. The hydrogenation of lactic acid is preferably conducted in neutral to acidic conditions since it is believed that these conditions will avoid lactate formation. A sample of results of this testing is summarized in FIGS. 11–12. As can be seen, in a flow reactor, conversion increases with temperature while selectivity decreases. Under the flow reactor conditions tested, it was surprisingly discovered that increasing hydrogen pressure increased both yield and selectivity while increasing the excess of $H_2$ to lactic acid had no significant effect on either conversion or selectivity. Pressure during hydrogenation of lactic acid is preferably above 2100 psi (15 MPa), more preferably above 2300 psi (16 MPa), and in some embodiments 16–35 MPa. The higher pressure appears to reduce the over-reduction to ethanol.

Closure

While preferred embodiments of the present invention have been shown and described, it will be apparent to those skilled in the art that many changes and modifications may be made without departing from the invention in its broader aspects. The appended claims are therefore intended to include all such changes and modifications as fall within the true spirit and scope of the invention.

We claim:

1. A hydrogenolysis method comprising:
   reacting a composition with hydrogen, at a temperature of at least 120° C., and in the presence of a solid catalyst;
   wherein the composition comprises a component selected from the group consisting of: a 6 carbon sugar, a 6 carbon sugar alcohol; and glycerol; and
   wherein the solid catalyst comprises rhenium and nickel.

2. A hydrogenolysis method comprising:
   reacting a composition with hydrogen, at a temperature of at least 120° C., and in the presence of a solid catalyst;
   wherein the composition comprises a 6 carbon sugar, or a 6 carbon sugar alcohol;
   wherein the solid catalyst comprises a multimetallic catalyst comprising rhenium and at least one member selected from the group consisting of Ni, Pd, Co, Ag, Au, Rh, Pt, Ir, Os, and Cu; and
   wherein the carbon molar selectivity to PG is at least 30%.

3. The method of claim 2 wherein the multimetallic catalyst comprises nickel.

4. The method of claim 3 wherein the method comprises a continuous conversion of a 6-carbon sugar alcohol and the solid catalyst comprises rhenium and nickel.

5. The method of claim 4 wherein the PG selectivity is in the range of 30 to 40%.

6. A hydrogenolysis method comprising:
   passing a composition into a reaction chamber;
   reacting the composition with hydrogen, at a temperature of at least 120° C., and in the presence of a solid catalyst;
   wherein the composition comprises glycerol and wherein, prior to passing the composition into the reaction chamber, glycerol is present in higher molar concentration than sugars or sugar alcohols; and
   wherein the solid catalyst comprises a multimetallic catalyst comprising rhenium and at least one member selected from the group consisting of Ni, Pd, Co, Ag, Au, Rh, Pt, Ir, Os, and Cu.

7. A hydrogenolysis method comprising:
   reacting a composition with hydrogen, at a temperature in the range of 120 to 190° C., and in the presence of a solid catalyst;
   wherein the composition comprises a component selected from the group consisting of: a 6 carbon sugar, a 6 carbon sugar alcohol; and glycerol; and
   wherein the solid catalyst comprises a multimetallic catalyst comprising rhenium and at least one member selected from the group consisting of Ni, Pd, Co, Ag, Au, Rh, Pt, Ir, Os, and Cu.

8. The method of claim 7 wherein the method comprises a continuous conversion of a 6-carbon sugar alcohol and the solid catalyst comprises rhenium and nickel.

9. The method of claim 8 wherein the 6-carbon sugar alcohol is in aqueous solution and the solid catalyst comprises a carbon support.

10. The method of claim 8 wherein the 6-carbon sugar alcohol is in aqueous solution in basic conditions.

11. A composition of matter comprising:
    a solid nickel and rhenium-containing catalyst;
    water, hydrogen; and
    a component selected from the group consisting of: a 6 carbon sugar, a 6 carbon sugar alcohol; and glycerol.

12. The composition of claim 11 wherein the solid catalyst comprises a carbon support.

13. The composition of claim 11 wherein the water has a basic pH.

14. The composition of claim 11 wherein the catalyst contains 0.5 to 2.5 weight % rhenium and 1 to 10 weight % nickel.

15. The composition of claim 11 comprising 20 to 50 weight % of said component.

16. A method of improving the catalytic activity or selectivity of a supported metal catalyst for the hydrogenolysis of a 6-carbon sugar, 6-carbon sugar alcohol, or glycerol comprising:
    incorporating rhenium in a nickel-containing metal catalyst to form a rhenium-containing multimetallic metal catalyst; and
    exposing said sugar or sugar alcohol to said rhenium-containing multimetallic metal catalyst under conditions sufficient to convert at least 40% of said sugar, sugar alcohol, or glycerol to propylene glycol, glycerol, ethylene glycol or any combination thereof;
    wherein improving means that when tested with a 20 weight % glycerol in aqueous solution with 2 weight % sodium hydroxide, 1200 psi (8.2 MPa) hydrogen in a batch reactor for four hours, the yield of PG is improved by at least 5%, as compared with running the same reaction under the same conditions over each of: the same catalyst without rhenium, the same catalyst without rhenium but containing added weight of metal equal to the weight of rhenium in the improved method, and the same catalyst without rhenium but containing added moles of metal equal to the moles of rhenium in the improved method.

17. A method of improving the reaction of hydrogen with a composition, comprising:

exposing the composition to hydrogen in the presence of a solid, multimetallic catalyst comprising rhenium and at least one member selected from the group consisting of Ni, Pd, Co, Ag, Au, Rh, Pt, Ir, Os, and Cu;

wherein the composition comprises a component selected from the group consisting of: a 6 carbon sugar, a 6 carbon sugar alcohol, and glycerol; and converting at least 80% of said component to lower molecular weight products including propylene glycol (PG);

wherein improving means that at the same conditions where the rhenium-containing multimetallic catalyst results in said at least 80% conversion, the yield of PG is improved by at least 5%, as compared with running the same reaction over each of: the same catalyst without rhenium, the same catalyst without rhenium but containing added weight of metal equal to the weight of rhenium in the improved method, and the same catalyst without rhenium but containing added moles of metal equal to the moles of rhenium in the improved method.

18. A method of hydrogenolysis of an oxygen-containing organic compound, comprising:

reacting an aqueous composition with hydrogen at a temperature of at least 120° C., and in the presence of a solid catalyst;

wherein the aqueous composition comprises water and an oxygen-containing organic compound, where the solid catalyst comprises nickel and rhenium, and wherein at least 25% as much C—O hydrogenolysis occurs as C—C hydrogenolysis.

19. The method of claim 18 wherein the C—O hydrogenolysis and C—C hydrogenolysis occur simultaneously.

20. The method of claim 18 wherein the C—C hydrogenolysis occurs first, base is added, and the C—O hydrogenolysis is then conducted.

21. The method of claim 18 wherein the composition comprises a component selected from the group consisting of: a 6 carbon sugar, a 6 carbon sugar alcohol, and glycerol.

22. The method of claim 21 wherein the method comprises a continuous conversion of a 6-carbon sugar alcohol.

23. The method of claim 21 wherein the reaction occurs in a temperature range of 120 to 190° C.

24. A method of hydrogenolysis of an oxygen-containing organic compound, comprising:

reacting an aqueous composition with hydrogen in a temperature range of 120 to 190° C., and in the presence of a solid catalyst;

wherein the aqueous composition comprises water and an oxygen-containing organic compound, where the solid catalyst comprises a multimetallic catalyst comprising rhenium and at least one member selected from the group consisting of Ni, Pd, Co, Ag, Au, Rh, Pt, Ir, Os, and Cu, and wherein there is at least 25% as much C—O hydrogenolysis occurs as C—C hydrogenolysis.

25. The method of claim 24 wherein the multimetallic catalyst comprises nickel.

26. The method of claim 25 wherein the solid catalyst comprises a carbon support.

27. A method of making 1,3-propanediol comprising:

reacting a composition comprising glycerol with hydrogen at a temperature of at least 120° C., and in the presence of a solid multimetallic catalyst in neutral or acidic conditions, the multimetallic catalyst comprising rhenium and at least one member selected from the group consisting of Ni, Pd, Co, Ag, Au, Rh, Pt, Ir, Os, and Cu.

28. The method of claim 27 wherein the glycerol is in aqueous solution and the selectivity to 1,3-propanediol is at least 2%.

29. The method of claim 27 wherein the multimetallic catalyst comprises nickel.

30. The method of claim 27 wherein the multimetallic catalyst comprises palladium.

31. The method of claim 27 wherein the multimetallic catalyst further comprises Ru.

* * * * *

UNITED STATES PATENT AND TRADEMARK OFFICE
CERTIFICATE OF CORRECTION

PATENT NO. : 6,841,085 B2
APPLICATION NO. : 10/000836
DATED : January 11, 2005
INVENTOR(S) : Werpy et al.

It is certified that error appears in the above-identified patent and that said Letters Patent is hereby corrected as shown below:

Column 8, line 65 – Replace "$(W_{NiNo3})$" with --$(W_{NiO3})$--.

Column 9, line 23 – Replace "80 C" with --80° C--.

Column 15 and 16, Table 8 – Insert the following title above Table 8 -- Arabinitol-1 Conversion Data Catalyst Description: 2.5%Ni 2.5% Re / 120% CTC (CCC) Carbon (Temp.= 200 C ; 1200 PSIG)--.

Signed and Sealed this

Tenth Day of April, 2007

JON W. DUDAS
*Director of the United States Patent and Trademark Office*